United States Patent
Ito

(10) Patent No.: US 9,250,221 B2
(45) Date of Patent: Feb. 2, 2016

(54) STANDARD SAMPLE AND METHOD OF PREPARING SAME

(71) Applicant: KABUSHIKI KAISHA TOSHIBA, Minato-Ku, Tokyo (JP)

(72) Inventor: Shoko Ito, Kawasaki (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 0 days.

(21) Appl. No.: 14/172,662

(22) Filed: Feb. 4, 2014

(65) Prior Publication Data

US 2015/0059496 A1 Mar. 5, 2015

(30) Foreign Application Priority Data

Sep. 3, 2013 (JP) .................. 2013-181965

(51) Int. Cl.
*G01N 1/40* (2006.01)
*G01N 33/00* (2006.01)

(52) U.S. Cl.
CPC .............. *G01N 33/00* (2013.01); *G01N 1/4055* (2013.01); *G01N 1/4077* (2013.01); *G01N 2001/4027* (2013.01)

(58) Field of Classification Search
None
See application file for complete search history.

(56) References Cited

U.S. PATENT DOCUMENTS

| 5,395,446 A | 3/1995 | Kageyama et al. |
| 5,686,314 A * | 11/1997 | Miyazaki ...................... 436/177 |
| 7,692,782 B2 | 4/2010 | Nolot |
| 2007/0298181 A1* | 12/2007 | Kojima et al. ................ 427/401 |
| 2014/0014138 A1* | 1/2014 | Spiegelman et al. ........... 134/31 |

FOREIGN PATENT DOCUMENTS

| JP | 03-255929 A | 11/1991 |
| JP | 06-011451 A | 1/1994 |
| JP | 09-072836 A | 3/1997 |
| JP | 11-145230 A | 5/1999 |
| JP | 3399671 B2 | 4/2003 |

* cited by examiner

*Primary Examiner* — Robert R Raevis
(74) *Attorney, Agent, or Firm* — Holtz, Holtz & Volek PC

(57) ABSTRACT

In one embodiment, a method of preparing a standard sample includes forming a second layer containing an analysis target element on a substrate via a first layer. The method further includes dissolving the first and second layers to form a plurality of droplets containing the analysis target element on the substrate. The method further includes drying the droplets to form a plurality of particles containing the analysis target element on the substrate.

18 Claims, 4 Drawing Sheets

| ANALYSIS SAMPLE | CONCENTRATION (atoms/cm$^2$) | | | σ | |
|---|---|---|---|---|---|
| | BEFORE CORRECTION | AFTER CORRECTION | CHEMICAL ANALYSIS VALUE | BEFORE CORRECTION | AFTER CORRECTION |
| A | 2.1×10$^{15}$ | 2.1×10$^{15}$ | 2.1×10$^{15}$ | 1.5 | 0.7 |
| B | 2.0×10$^{15}$ | 2.1×10$^{15}$ | 2.1×10$^{15}$ | 1.3 | 0.8 |

FIG.5

STANDARD SAMPLE AND METHOD OF PREPARING SAME

CROSS REFERENCE TO RELATED APPLICATION

This application is based upon and claims the benefit of priority from the prior Japanese Patent Application No. 2013-181965, filed on Sep. 3, 2013, the entire contents of which are incorporated herein by reference.

FIELD

Embodiments described herein relate to a standard sample and a method of preparing the same.

BACKGROUND

In recent years, research and development have been examined on a nanodot memory which is fabricated by, for example, forming a charge storage layer or the like of a memory cell by using particle substances referred to as nanodots. In order to conduct the research and development on the nanodot memory, there is a need to analyze properties of the nanodots by a physical or chemical analysis method. In the physical analysis method, it is often the case that analytical data is measured by beam measurement or the like, and then the measurement result on an analysis sample is compared with the measurement result on a standard sample which serves as an analysis criterion. However, this type of existing physical analysis method generally supposes that the analysis sample and the standard sample have the analysis target substances of thin films. Therefore, when the existing physical analysis method is applied to the analysis sample including the nanodots as the analysis target substances, there is a possibility of failing to obtain accurate results of the analysis. On the other hand, the chemical analysis method of dissolving the substances to be analyzed is not affected by the shapes of the substances before the dissolution. However, the chemical analysis method cannot be applied to the nanodots containing an element which is difficult to be dissolved like noble metal elements.

BRIEF DESCRIPTION OF THE DRAWINGS

FIG. 5 is a table showing results of analyzing analysis samples by using the standard sample of the first embodiment.

DETAILED DESCRIPTION

Embodiments will now be explained with reference to the accompanying drawings.

In one embodiment, a method of preparing a standard sample includes forming a second layer containing an analysis target element on a substrate via a first layer. The method further includes dissolving the first and second layers to form a plurality of droplets containing the analysis target element on the substrate. The method further includes drying the droplets to form a plurality of particles containing the analysis target element on the substrate.

First Embodiment

FIGS. 1A to 2C are cross-sectional views illustrating a method of preparing a standard sample of a first embodiment. The standard sample of the present embodiment is used, for example, for physical analysis of an analysis sample including nanodots as analysis target substances.

Figure 1A:
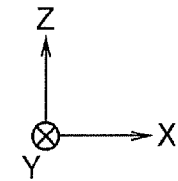
FIGS. 1A to 2C are cross-sectional views illustrating a method of preparing a standard sample of a first embodiment.
Figure 1A:

First, as shown in FIG. 1A, a chemical oxide film 2 is formed on a surface of a substrate 1 by using a mixed solution (SC-2) of hydrochloric acid and hydrogen peroxide water. The substrate 1 is, for example, a silicon substrate. The chemical oxide film 2 is, for example, a silicon oxide film formed by oxidizing the surface of a silicon substrate. The chemical oxide film 2 is an example of a first layer. The first layer may be a native oxide film formed by native oxidation of the surface of the substrate 1.

FIG. 1A shows X and Y directions which are parallel to the surface of the substrate 1 and perpendicular to each other, and a Z direction which is perpendicular to the surface of the substrate 1. In this specification, the +Z direction is treated as an upward direction, whereas the −Z direction is treated, as a downward direction. For example, the positional relationship between the substrate 1 and the chemical oxide film 2 is described as the substrate 1 located under the chemical oxide film 2.

Figure 1B:
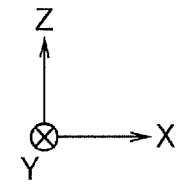
Figure 1B:
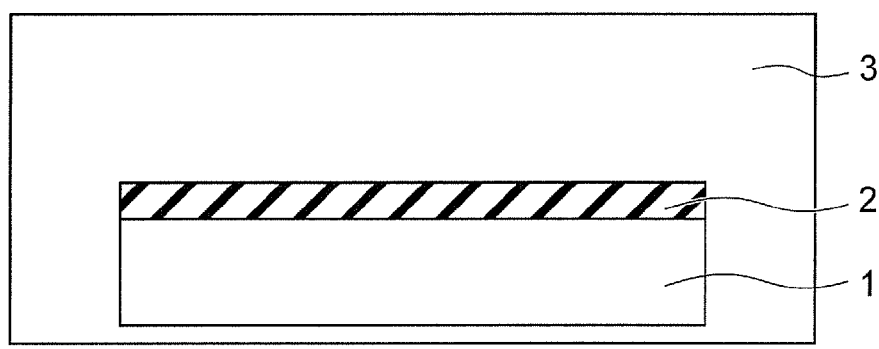

Next, as shown in FIG. 1B, the substrate 1 is immersed for 60 seconds in a Fe (iron) solution 3 of known concentration (for example, 20 ppm). Fe is an example of an analysis target element. The Fe solution 3 is produced, for example, by diluting a standard stock solution (1000 ppm) for atomic absorption spectroscopy to 1/50. When there are N types of analysis target elements (N is an integer of 2 or more), the substrate 1 is immersed in a solution containing the N types of elements. Examples of the analysis target element include a noble metal element such as Au (gold) or Pt (platinum).

Figure 1C:
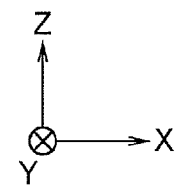
Figure 1C:
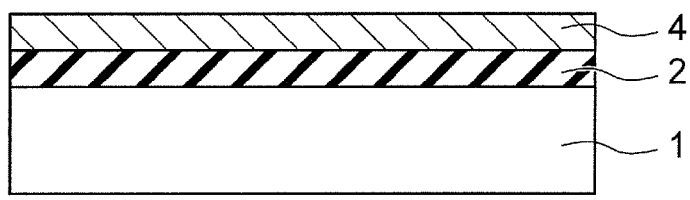

Next, as shown in FIG. 1C, the substrate 1 after the immersion is dried by spin drying without rinsing to form a Fe layer 4 on the surface of the substrate 1 via the chemical oxide film 2. The Fe layer 4 is an example of a second layer. It is possible to form the Fe layer 4 which has a desired Fe atom concentration by controlling the Fe atom concentration of the Fe solution 3, because the concentration of Fe atoms in the Fe layer 4 is primarily determined by the concentration of Fe atoms in the Fe solution 3. The Fe atom concentration of the Fe layer 4 of the present embodiment is set to, for example, $3 \times 10^{13}$ atoms/cm$^{-2}$.

Instead of the immersion method, the Fe layer 4 may be formed by a spin coat method of coating the surface of the substrate 1 with the Fe solution 3 of known concentration via the chemical oxide film 2. The spin coat method has an advantage of being able to form the Fe layer 4 on only one main surface of the substrate 1. On the other hand, the immersion method has an advantage of being able to form the Fe layer 4 with in-plane uniformity. In addition, the Fe layer 4 may be formed by chemical vapor deposition (CVD) or physical vapor deposition (PVD).

Figure 2A:
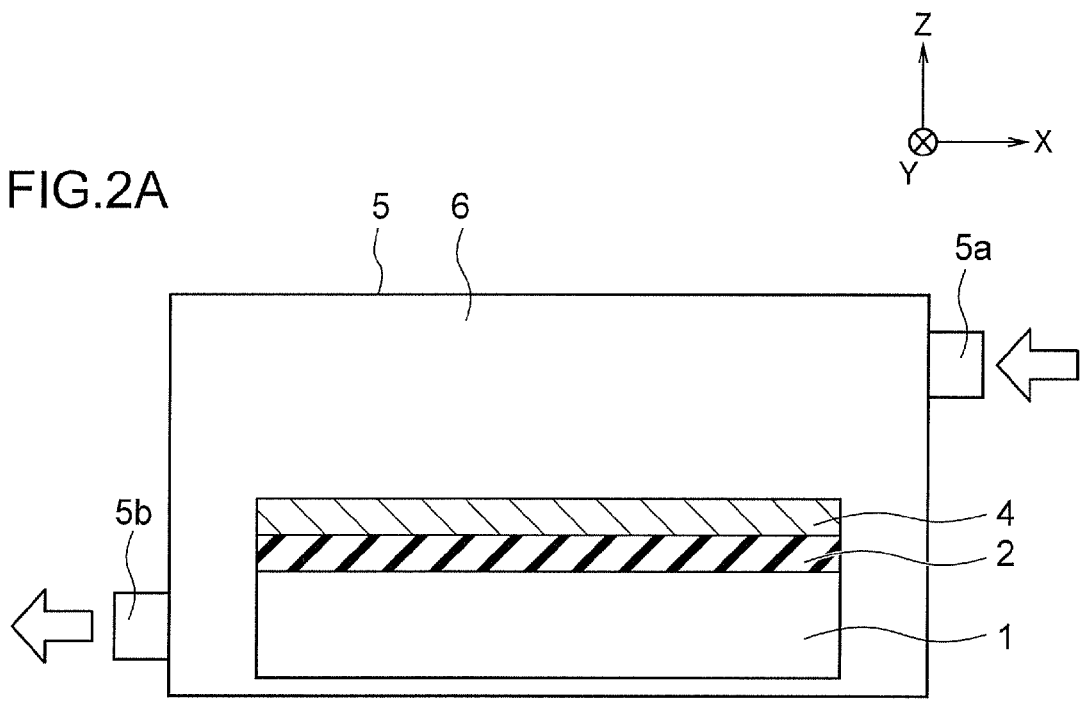

Next, as shown in FIG. 2A, the substrate 1 is housed in an airtight container 5 formed of Teflon™ to expose the substrate 1 to a hydrogen fluoride (HF) gas 6 for 30 minutes. The HF gas 6 is an example of a dissolving gas. Reference numerals 5a and 5b respectively denote a gas supply port and a gas exhaust port of the airtight container 5.

In the step of FIG. 2A, the Fe layer 4 is exposed to the HF gas 6 and dissolved. Furthermore, the chemical oxide film 2 is exposed to the HF gas 6 and dissolved. As a result, the Fe layer 4 and the chemical oxide film 2 are completely dissolved to expose the surface of the substrate 1 again.

Figure 2B:
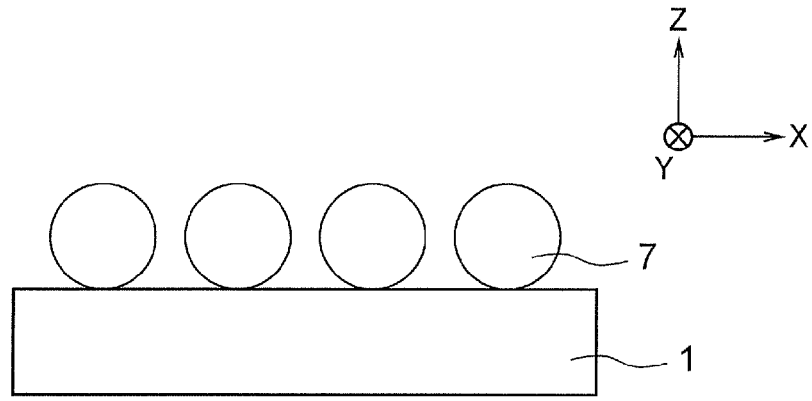

In a case where the substrate 1 is a silicon substrate, a plurality of droplets 7 are formed on the surface of the substrate 1 as a result of the step in FIG. 2A, because silicon is hydrophobic (FIG. 2B). The droplets 7 contain Fe derived from the Fe layer 4, and $H_2SiF_6$ and $H_2O$ derived from the chemical oxide film 2 and the HF gas 6.

The substrate 1 may be exposed to a mixed gas containing the HF gas 6 in the step of FIG. 2A. Examples of a gas contained in this mixed gas include an inert gas such as a nitrogen gas, an argon gas, and a helium gas, dry air, and water vapor. In addition, the dissolving gas may be any gas other than the HF gas 6, which is capable of dissolving the Fe layer 4 and the chemical oxide film 2.

Figure 2C:
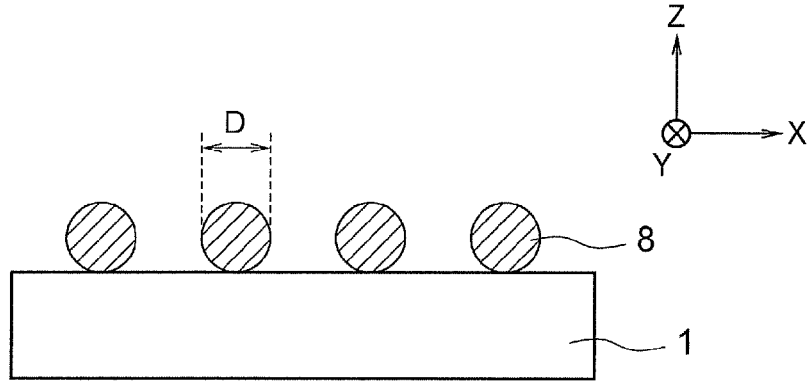

Next, as shown in FIG. 2C, the droplets 7 are dried to evaporate the $H_2SiF_6$ and $H_2O$ in the droplets 7, and to form a plurality of Fe solid particles 8 on the surface of the substrate 1. In this way, the standard sample of the present embodiment is prepared. The Fe particles 8 are an example of particles containing the analysis target element. The method of preparing the standard sample of the present embodiment provides the Fe particles 8 to have approximately spherical shapes, and to have diameters D on the order of 1 nm to 1000 nm. This method may provide a few Fe particles 8 having diameters D of sub-nm and several μm. If these Fe particles 8 are took in consideration, the diameters D of the Fe particles 8 provided by this method are on the order of 0.1 nm to 10 μm.

Figure 3:
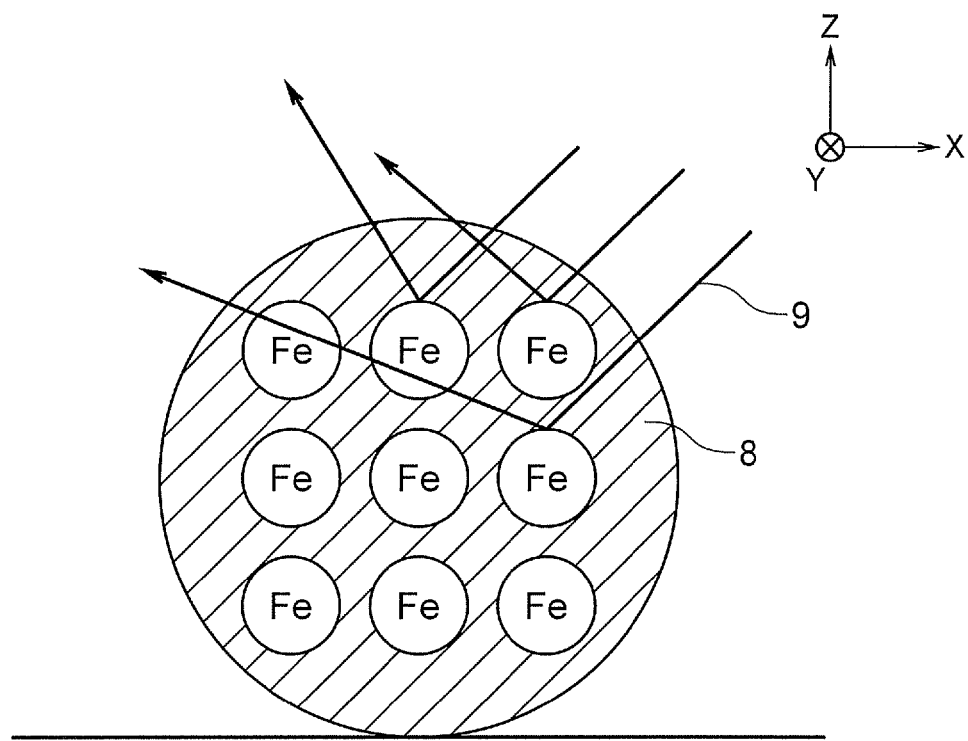
FIG. 3 is a cross-sectional view conceptually illustrating a structure of a Fe particle prepared by the method of preparing the standard sample of the first embodiment.

FIG. 3 is a cross-sectional view conceptually illustrating a structure of a Fe particle 8 prepared by the method of preparing the standard sample of the first embodiment.

The Fe particle 8 is formed almost only by the Fe element, and has an approximately spherical shape. Reference numeral 9 denotes an analytical beam which is used to irradiate the Fe particle 8. The analytical beam 9 is regularly scattered when a Fe thin film is irradiated with the analytical beam 9, whereas the analytical beam 9 is scattered in various directions when the Fe particle 8 is irradiated with the analytical beam 9.

In a case of carrying out physical analysis of an analysis sample including nanodots as analysis target substances, the analytical beam 9 used to irradiate the nanodots is scattered in various directions as in the case of irradiating the Fe particle 8 with the analytical beam 9. Therefore, according to the present embodiment, the standard sample prepared by the steps in FIGS. 1A to 2C is used to carry out the physical analysis of the analysis sample including the nanodots as the analysis target substances, thereby making it possible to carry out precise analysis of the analysis sample.

Examples of the physical analysis method which is applicable to the present embodiment include a Rutherford backscattering spectrometry (RBS) method. In the RBS method, a high-speed ion beam is used as the analytical beam 9. According to the RBS method, the elemental composition of the analysis sample can be obtained by making use of the fact that the amount of ion energy change with elastic scattering on atomic nuclei in the analysis sample varies depending on the mass and location of the nuclei.

The standard sample of the present embodiment also can be used for physical analysis of the analysis sample including particles other than the nanodots as the analysis target substances.

Figure 4:
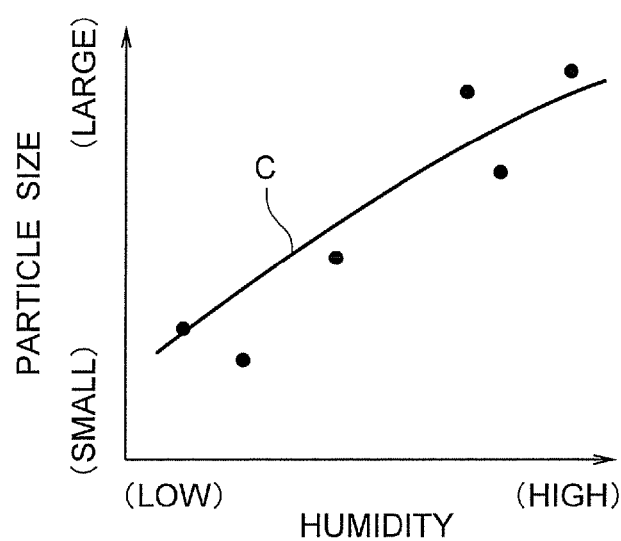
FIG. 4 is a graph showing a relationship between humidity and particle sizes (diameters D) of Fe particles prepared by the method of preparing the standard sample of the first embodiment.

FIG. 4 is a graph showing a relationship between humidity and particle sizes (diameters D) of the Fe particles 8 prepared by the method of preparing the standard sample of the first embodiment. The humidity in FIG. 4 indicates humidity in the airtight container 5 when the step in FIG. 2A is carried out.

The points shown in FIG. 4 indicate the results of measuring the humidity and the particle sizes of the Fe particles 8. In addition, the curve C shown in FIG. 4 indicates an approximate curve calculated by a least squares method on the basis of these points. From the graph in FIG. 4, it is understood that the particle sizes of the Fe particles 8 are decreased as the humidity is lower, and increased as the humidity is higher. When the humidity is increased to the extent that the atmosphere in the airtight container 5 is saturated, the particle sizes of the Fe particles 8 are increased to on the order of 1000 nm.

Therefore, according to the present embodiment, the particle sizes of the Fe particles 8 can be controlled by adjusting the humidity in the airtight container 5. For example, when there is a desire to prepare the Fe particles 8 which are small in particle size, the inside of the airtight container 5 is adjusted to a low-humidity environment. On the other hand, when there is a desire to prepare the Fe particles 8 which are large in particle size, the inside of the airtight container 5 is adjusted to a high-humidity environment.

The low-humidity environment can be achieved, for example, by flowing a gas from a hydrogen fluoride (HF) aqueous solution bubbled with nitrogen ($N_2$) to the airtight container 5, thereby supplying the HF gas 6 into the airtight container 5. On the other hand, the high-humidity environment can be achieved by using, as the HF gas 6, an HF gas evaporated from an HF aqueous solution still standing in the airtight container 5, for example.

FIG. 5 is a table showing results of analyzing analysis samples by using the standard sample of the first embodiment.

FIG. 5 shows results of analyzing two analysis samples A and B including nanodots as analysis target substances. The nanodots of the analysis sample A and the nanodots of the analysis sample B were prepared by carrying out a heat treatment at different temperatures. The RBS method was adopted as the physical analysis method on the analysis samples A and B.

The uncorrected concentration (concentration before correction) indicates the nanodot concentration measured by using a standard sample including a thin film as an analysis target substance. The corrected concentration (concentration after correction) indicates the nanodot concentration measured by using a standard sample including particles as analysis target substances. The latter case was carried out by using, as the standard sample, a sample prepared by using a low-humidity environment in the steps in FIGS. 1A to 2C. The chemical analysis value indicates the nanodot concentration calculated by a chemical analysis method.

The uncorrected concentrations, corrected concentrations, and chemical analysis values on the analysis samples A and B are each an average value of measurement values obtained by measurement conducted more than once. The uncorrected σ and the corrected σ respectively indicate standard deviations (variations) for the measurement values of the uncorrected concentration and corrected concentration.

It is understood from FIG. 5 that the use of the standard sample including the particles as the analysis target substances makes the measurement values of the concentrations closer to the concentrations of chemical analysis values (which are considered close to the true values), as compared with the case of using the standard sample including the thin film as the analysis target substance. Furthermore, it is understood that the use of the standard sample including the particles as the analysis target substance reduces the variations for the measurement values of the concentrations, as compared with the case of using the standard sample including the thin film as the analysis target substance.

As described above, the method of preparing the standard sample of the present embodiment forms the Fe layer 4 on the substrate 1 via the chemical oxide film 2, dissolves the chemical oxide film 2 and the Fe layer 4 to form the plurality of droplets 7 on the substrate 1, and dries the droplets 7 to form the plurality of Fe particles 8 on the substrate 1. More specifically, the method of preparing the standard sample of the present embodiment forms the plurality of particles 8 containing the analysis target element on the substrate 1 in accordance with the steps described above.

Therefore, the present embodiment can provide a standard sample capable of precise analysis on an analysis sample including particles as analysis target substances.

For example, the use of the standard sample of the present embodiment, which has the particles as the analysis target substance, makes it possible to obtain accurate measurement values with small variations, as compared with a case of using a standard sample including a thin film as an analysis target substance.

While certain embodiments have been described, these embodiments have been presented by way of example only, and are not intended to limit the scope of the inventions. Indeed, the novel samples and methods described herein may be embodied in a variety of other forms; furthermore, various omissions, substitutions and changes in the form of the samples and methods described herein may be made without departing from the spirit of the inventions. The accompanying claims and their equivalents are intended to cover such forms or modifications as would fall within the scope and spirit of the inventions.

The invention claimed is:

1. A method of preparing a standard sample, the method comprising:
    forming a second layer containing an analysis target element on an entirety of an upper surface of a first layer which is formed on a substrate;
    dissolving the first and second layers to form a plurality of droplets containing the analysis target element on the substrate; and
    drying the droplets to form a plurality of particles containing the analysis target element on the substrate.

2. The method of claim 1, wherein the first and second layers are dissolved by exposing the first and second layers to a dissolving gas.

3. The method of claim 2, wherein the dissolving gas contains hydrogen fluoride.

4. The method of claim 3, wherein the dissolving gas is a mixed gas containing the hydrogen fluoride.

5. The method of claim 4, wherein the mixed gas contains an inert gas, air, or water vapor.

6. The method of claim 1, wherein the first layer is a chemical oxide film or a native oxide film.

7. The method of claim 6, wherein the chemical oxide film is formed by oxidizing a surface of the substrate.

8. The method of claim 1, wherein the analysis target element includes a metal element.

9. The method of claim 1, wherein the second layer is formed by immersing the substrate in a liquid containing the analysis target element.

10. The method of claim 1, wherein the second layer is formed by coating a surface of the substrate with a liquid containing the analysis target element.

11. The method of claim 1, wherein diameters of the particles are 0.1 nm to 10 µm.

12. The method of claim 1, wherein diameters of the particles are 1 nm to 1000 nm.

13. The method of claim 1, wherein the analysis target element is a noble metal element.

14. The method of claim 13, wherein the noble target element is Au (gold) or Pt (platinum).

15. The method of claim 1, wherein the analysis target element is Fe (iron).

16. The method of claim 1, wherein the first and second layers are dissolved by using a mixed solution of hydrochloric acid and hydrogen peroxide water.

17. The method of claim 1, wherein each of the plurality of particles contains the analysis target element.

18. The method of claim 1, wherein the plurality of particles are used as the standard sample for a physical analysis performed by irradiating the standard sample with a beam.

* * * * *